United States Patent
Douglas et al.

(10) Patent No.: US 10,912,874 B2
(45) Date of Patent: Feb. 9, 2021

(54) INTRACARDIAC PUMP

(71) Applicants: Robert E Douglas, Winter Park, FL (US); Kathleen M Douglas, Winter Park, FL (US)

(72) Inventors: Robert E Douglas, Winter Park, FL (US); Kathleen M Douglas, Winter Park, FL (US)

(*) Notice: Subject to any disclaimer, the term of this patent is extended or adjusted under 35 U.S.C. 154(b) by 0 days.

(21) Appl. No.: 16/439,972

(22) Filed: Jun. 13, 2019

(65) Prior Publication Data
US 2019/0388597 A1 Dec. 26, 2019

Related U.S. Application Data

(60) Provisional application No. 62/689,861, filed on Jun. 26, 2018.

(51) Int. Cl.
*A61M 1/10* (2006.01)
*A61N 1/05* (2006.01)
(Continued)

(52) U.S. Cl.
CPC ........ *A61M 1/1074* (2014.02); *A61M 1/1005* (2014.02); *A61M 1/106* (2013.01); *A61M 1/1008* (2014.02); *A61M 1/1044* (2014.02); *A61M 1/1055* (2014.02); *A61M 1/1086* (2013.01); *A61M 1/122* (2014.02);
(Continued)

(58) Field of Classification Search
CPC ..... A61B 5/042; A61B 5/6853; A61B 5/6858; A61B 2017/00243; A61B 5/026; A61N 1/3627; A61N 1/3684; A61N 1/08; A61N 1/3622; A61N 1/362; A61M 1/1086; A61M 1/122; A61M 1/12; A61M 2230/04; A61M 1/1074; A61M 1/1005; A61M 1/1072; A61M 1/125; A61M 2230/06; A61M 2230/63
See application file for complete search history.

(56) References Cited

U.S. PATENT DOCUMENTS 4,652,265 A * 3/1987 McDougall ........... A61M 1/106 623/24
4,902,273 A * 2/1990 Choy .................... A61M 1/122 600/18

(Continued)

FOREIGN PATENT DOCUMENTS

WO    WO 9966969    12/1999

*Primary Examiner* — Deborah L Malamud

(57) ABSTRACT

An intra-cardiac device component (ICDC) is inserted into one to four chambers of the heart. The ICDC in the right atrium and left atrium expands while the tricuspid and mitral valves are open during the first-time epoch. The expansion in the right atrium and left atrium pushes blood from these atriums into their respective ventricles. The ICDC in the right ventricle and left ventricle contracts at this time epoch and the pulmonary and aortic valves are closed. In the succeeding time epoch, the ICDC in the right atrium and left atrium contracts while the tricuspid and mitral valves are closed, and the right atrium and left atrium are filling with blood. The ICDC in the right ventricle and left ventricle expand in this time epoch while the pulmonary and aortic valves are open. This sequence increases blood flow into the pulmonary artery and aorta and helps to remedy the decreased ability to pump blood in heart failure patients.

26 Claims, 18 Drawing Sheets

| Structure | Goal pressure Range in mmHg |
|---|---|
| Right Atrium | 2-8 |
| Right Ventricle | 15-30 systolic / 2-8 diastolic |
| Pulmonary Artery | 15-30 systolic / 4-12 diastolic |
| Left Atrium | 2-10 |
| Left Ventricle | 100-140 systolic / 3-12 diastolic |
| Aorta | 100-140 systolic / 60-90 diastolic |

(51) Int. Cl.
*A61N 1/362* (2006.01)
*A61M 1/12* (2006.01)

(52) U.S. Cl.
CPC ............ *A61M 1/127* (2013.01); *A61N 1/056* (2013.01); *A61N 1/362* (2013.01); *A61M 2205/054* (2013.01); *A61M 2205/3344* (2013.01); *A61M 2205/3375* (2013.01); *A61M 2205/3379* (2013.01); *A61M 2205/52* (2013.01); *A61M 2205/8206* (2013.01); *A61M 2230/06* (2013.01); *A61M 2230/63* (2013.01)

(56) References Cited

U.S. PATENT DOCUMENTS

| | | |
|---|---|---|
| 5,722,429 A | 3/1998 | Larson |
| 5,820,542 A | 10/1998 | Dobak |
| 6,997,192 B2 | 2/2006 | Doke et al. |
| 8,670,842 B1 | 3/2014 | Bornzin et al. |
| 2004/0059348 A1 | 3/2004 | Geske |
| 2007/0150009 A1 | 6/2007 | Kveen |
| 2015/0038770 A1 | 2/2015 | Colella |
| 2017/0128013 A1 | 5/2017 | Kardium |
| 2017/0209688 A1 | 7/2017 | Drake et al. |

\* cited by examiner

| Intra-Cardiac Device Component (ICDC) phase | Volume inside of External Casing of ICDC (in mL) | Volume of compressible material within ICDC (in mL) | Volume of non-compressible material within ICDC (in mL) | Intra-CardiacDevice Component desired pressure (in mmHg) |
|---|---|---|---|---|
| Expanded | 50 | 45 | 5 | ~120 mmHg |
| Shrunken | 10 | 5 | 5 | 0-5 mmHg |

| Structure | Goal pressure Range in mmHg |
|---|---|
| Right Atrium | 2-8 |
| Right Ventricle | 15-30 systolic / 2-8 diastolic |
| Pulmonary Artery | 15-30 systolic / 4-12 diastolic |
| Left Atrium | 2-10 |
| Left Ventricle | 100-140 systolic / 3- 12 diastolic |
| Aorta | 100-140 systolic / 60-90 diastolic |

| Intra-Cardiac Device Component (ICDC) phase | Volume inside of External Casing of ICDC (in mL) | Volume of compressible material within ICDC (in mL) | Volume of non-compressible material within ICDC (in mL) | Intra-Cardiac Device Component desired pressure (in mmHg) |
|---|---|---|---|---|
| Expanded | 34 | 33 | 1 | ~15 mmHg |
| Shrunken | 4 | 3 | 1 | -120 mmHg |

Figure 17

INTRACARDIAC PUMP

TECHNICAL FIELD

Aspects of the present disclosure are generally related to medicine and more specifically heart failure.

BACKGROUND

Heart failure is a medical condition where the heart does not adequately pump blood to the organs of the body. One of the common causes is myocardial infarction (also known as heart attack) from coronary artery disease (narrowing of the blood vessels to the heart). During a myocardial infarction, a portion of the heart muscle dies off and the remaining heart muscle is overworked and progressively stretches out over time. The heart can enlarge and result in poor pumping ability. Coronary artery disease and myocardial infarction is just one of the many causes of heart failure. Other causes include high blood pressure, problems with heart valves, problems of the heart muscle (e.g., viral myocarditis, amyloidosis, HIV, arrythmia, sarcoidosis, etc.) and many others.

If there is right heart failure (due to pathology of the right atrium and right ventricle), then blood can back up into the organs of the body and patients can suffer from swelling in the legs. If there is left heart failure (due to pathology of the left atrium and left ventricle), then blood can back up into the lungs and patients can suffer from severe shortness of breath. Ultimately, depending on the cause, the heart failure may progress (i.e., pump failure worsens) and the condition can be lethal.

A left ventricular assist device (LVAD) is a battery-operated mechanical pump placed via an open-heart surgery procedure to treat end stage heart failure patients who are awaiting a heart transplant. The LVAD pulls blood from the left ventricle and sends it to the aorta, which then goes to the rest of the body. There are several limitations of the LVAD. First, the LVAD works as a pump only to support the left ventricle. Thus, other heart chambers are not supported. Second, it requires major open-heart surgery, which carries significant risks. Third, it requires a tube exiting the patient's skin connecting internal hardware to external hardware outside of the body. Thus, there are a set of challenges associated with the LVAD maintenance. Given these limitations, a better method and apparatus is needed to support patients who suffer from heart failure.

SUMMARY

All examples, aspects and features mentioned in this document can be combined in any technically possible way.

In accordance with an aspect of the invention a method comprises: inserting an intra-cardiac device component (for example, but not limited to an intra-cardiac device component for expansion/contraction) into each of the chambers of the heart. The intra-cardiac device component in the right atrium and left atrium would be expanding while the tricuspid and mitral valves are open during the first-time epoch. The intra-cardiac device component expansion in the right atrium and left atriums would push an increased flow of blood from these atriums into their respective ventricles. The intra-cardiac device component in the right ventricle and left ventricle would be contracting at this time epoch and the pulmonary and aortic valves are closed. Conversely, in the succeeding time epoch, the intra-cardiac device component in the right atrium and left atriums would be contracting while the tricuspid and mitral valves are closed. The intra-cardiac device component in the right ventricle and left ventricle would be expanding at this time epoch and the pulmonary and aortic valves open. This sequence would increase blood flow into pulmonary artery and aorta. The intra-cardiac device component would alternate expansion and contraction in successive epochs in accordance with the heart beats and functions of their respective chambers. The intra-cardiac device component would be emplaced in one to four chambers of the heart.

Some implementations comprise elements which include, but are not limited to, the following: intra-cardiac device component (ICDC); pressurized fluid bottle which stores fluid and passes it thru a tubular system to cause the ICDC to expand when fluid is inserted and contract when fluid is released; in/out tubes for pressurized fluid with valves to open/close to let air to enter ICDC or be released; storage element for the pressurized fluid; control mechanism which includes, but is not limited to: pressure gauge for tubes; computed system with algorithm for timing of the fluid/air input/output valve(s) to open/close during emptying (i.e., ejection phase) of blood from chamber(s) based on collected data (e.g., pressure, volume, rate, etc.); computer system with algorithm for timing of the fluid/air input/output valve(s) to open/close during filling of blood into the chamber(s) based on collected data (e.g., pressure, volume, rate, etc.); and power source preferably internal in the chest wall subcutaneous fat (note: if the system controller and power source are external to the body, these elements could be connected to local commercial power with a battery backup). In further implementation, desired ejection parameters (e.g., stroke volume, ejection fraction, etc.) could be modified by the intracardiac pump by analysis of multiple factors including but not limited to the following factors: valve opening size; duration of opening; and, heart chamber size.

Some implementations comprise a method to implant the ICDC and associated tubing including, but is not limited to, the following: entering the device into the body in proximity to and into Superior Vena Cava (SVC) and then following SVC to enter Right Atrium (RA); ICDC set 1 (IS1) is then inserted thru the inter-atrial septum separating the RA and Left Atrium (LA) such that: one ICDC would be in LA, one in the RA and ICDC connector in the inter-atrial septum; ICDC set 2 (IS2) is then inserted thru the RA and into Right Ventricle (RV) and moved to a position such that: ICDC set 2 could be inserted thru the inter-ventricular septum separating the RV and Left Ventricle (LV); one ICDC would be in RV, one in the LV and ICDC connector in the inter-ventricular septum. In continued implementation: connector tube(s) locations would include options: between the connectors of IS1 and IS2; between the connector of IS1 and external (or internal) fluid storage source; and between the connector of IS2 external (or internal) fluid storage source.

Some implementations comprise addition of one or more electrodes together with the afore described set of components. The purpose of these electrodes would be to stimulate and synchronize heart functioning in concert with the ICDC components. The rate of stimulation by the electrodes could be variable depending on the activity level of the patient.

Some implementations comprise a variation in the location of system elements. Example locations include, but are not limited to, the following: internal to the body as a self-contained unit, but with provision to replace power source; and ICDC internal to body and connector tubing and wiring both internal and external internal to the body and controller, fluid storage element and power source external to the body. In further implementation, if pressurized gas (e.g., air) is used as the mechanism to cause the ICDC to expand and the gas released when contraction occurs, a pressurized gas bottle could hold the gas external to the body and periodically be replaced when the stored gas was expended. If the fluid used as the mechanism to cause the ICDC to expand/contract is a liquid (e.g., saline solution), the fluid could be stored within a closed system.

Some implementations comprise a mechanism, other than fluid pressure differential, the cause the ICDC which include, but are not limited to, the following: for a closed system, a magnetized piston within the tubular system could connect the ICDC for right atrium (RA) and left atrium (LA) and the ICDC for right ventricle (RV) and left ventricle (LV) which would alternate electric current flow between magnets on the tubular system and permanent magnet on the piston. Current is provided alternating between magnets on the tubing and in synchronization with the heartbeat. Thus, the movement of the piston would push fluid into one ICDC and extract from the other during one-time epoch and reversed during the succeeding time epoch.

Some implementations comprise a mechanism, other than the ICDC to increase the blood flow out of the LV. This would include, but is not limited to, the following: a piston within a cylindrical-type shaped tube that is open at one end located within the LV. During the epochs wherein blood was entering the LV from the LA, the piston would be near the base of the cylinder. And, during the ejection epoch the piston would move forward toward the open end of the cylinder, thus pushing out the blood in the cylinder, thereby contributing to the volume of blood ejected during this time epoch. Further implementation could include, but is not limited to, the following: alternate electric current flow between magnets on the near ends of the cylinder and permanent magnet on the piston. Current is provided alternating between magnets on the cylinder in synchronization with the heartbeat. This option would obviate the need for external/internal storage of fluid.

Some implementations comprise a method to work in conjunction with a pacemaker, in present within the patient. The method includes, but is not limited to, the following: the signal emitted by the pacemaker could be detected by a sensor within the system and communicated to the controller element. The controller would then, in turn, synchronize the expansion/contraction of the ICDC accordingly. Note that without a pacemaker, the system controller would provide timing for the epochs of the expansion/contraction of the ICDCs.

Some implementations comprise a method to work in conjunction with a pressure sensor within the ICDC elements. The method includes, but is not limited to, the following: including a pressure sensor within the ICDC to sensing pressure and pressure changes within the chambers. This information would be transmitted to the controller and could be used to trigger expansion or contraction of the ICDC. The pressure data would also be available for diagnostic purposes.

Some implementations comprise a method to work in conjunction with a valve prosthesis within the heart. The ICDC in associated with the valve prosthesis to achieve coordinated movements during the valve prosthesis positioning. This method includes, but is not limited to, the following: mechanical connection between the ICDC and the valve prosthesis; electrical connection between the ICDC and the valve prosthesis; and, sensor system within the ICDC to detect the prosthetic valve position. Note: the ICDC may work in a similar fashion with a native heart valve to achieve synchronized movements.

Some implementations comprise a method to provide two (or more) levels of pressure for the ICDC. An example of a two levels of pressure system includes, but not limited to, the following: system could have a high-pressure element for the LV and a low-pressure element for the RA, LA, and RV. Separate tubing would pass the fluid of these two different pressure levels from their storage elements (i.e., high and low pressures) to respective ICDCs. This would accommodate approximate order of magnitude difference in pressure between these chambers.

Some implementations comprise a method to control the timing of the epochs. The duration of the epochs can be controlled by the controller element with manual input from the patient. Variables which could affect the timing include, but are not limited to, the following: the patient's activity level with a decrease in the time interval of an epoch corresponding to an increase in activity level; a selected epoch interval between activation of ICDC (e.g., on for two epochs and off for two epochs).

Some implementations comprise a method to provide a pre-installation planning process. From a 'systems' perspective, the volume of blood ejected from each of the chambers should be roughly equal (assuming there are no shunts). As an example, the total blood flow through the body could be limited due to the low ejection from the LV while the RA, RV, and LA might capable of increased blood volume flow. In this example scenario, the LV is the "rate-limiting step" for the flow to the whole body. With this stipulation, the pre-installation process could include, but is not limited to, the following: the pre-existing ejection parameters (e.g., end diastolic volume, end systolic volume, ejection fraction, etc.) can be calculated during an echocardiogram (or other imaging procedure) while examining heart functioning. Based on the size of the chamber, the current level of volume ejection for each chamber, the desired level of ejection, the size of the ICDC can be calculated to achieve the desired level of extraction as compared with the current level of ejection. This, in turn, would determine the size of the ICDC and the fluid flow rate into the ICDC.

Some implementations comprise a method to provide a check on system operation. This would include, but is not limited to, the following: the system could include an ultrasound monitor which would perform the function of performing an echo calculation of ejection volume for each chamber after installation and during operation of the system. This monitor could be linked to the system controller and adjustments, as necessary, in ICDC size for each chamber could be calculated and the control system would implement these needed adjustments.

Some implementations comprise a method to provide a capability within the system controller to generate a report regarding utilization of the system over the reporting period. Reporting elements could include, but are not limited to, the following: the report could: indicate ICDC size during each epoch for each chamber: associated ejection parameters (e.g., end systolic volume, end diastolic volume, ejection fraction, etc.) for each chamber for each epoch; and number of epochs; total ejection volume during the reporting period; and statistics regarding these measures. If pressure readings within the chambers were available, these could be included in the report. This information could be correlated with the patient's health and progress on metrics such as exercise performance. As the patient's overall health improves, the device parameters (e.g., ICDC size) for each epoch health could be adjusted.

BRIEF DESCRIPTION OF FIGURES

FIG. 17 quantifies volumetric displacement by an ICDC during expansion/contraction phases and internal pressure.

DETAILED DESCRIPTION OF FIGURES

Figure 1:
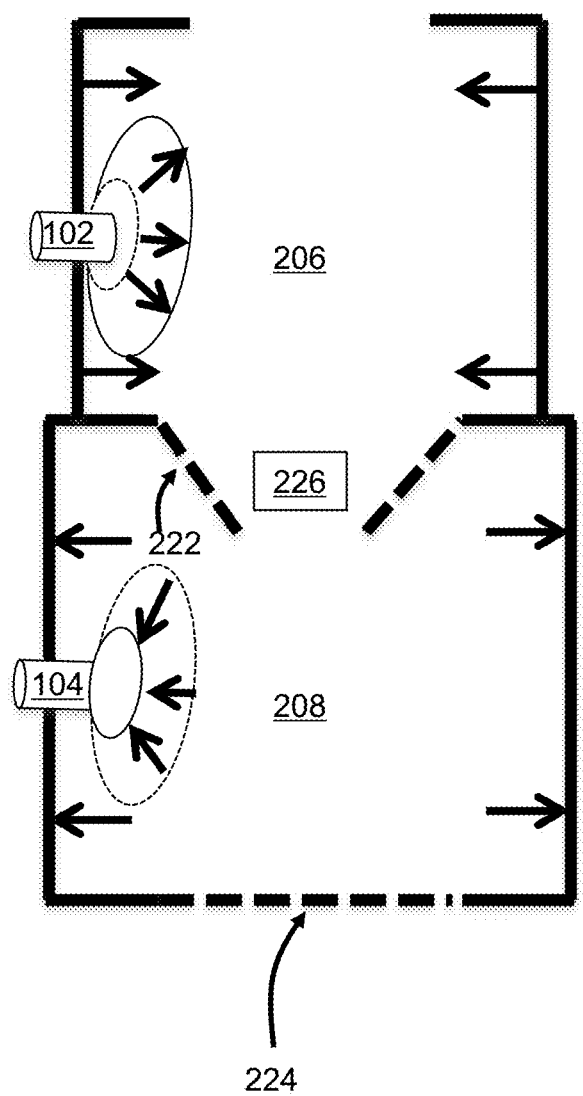
FIG. 1 illustrates oxygenated blood flowing into left ventricle assisted by an intra-cardiac device component.

FIG. 1 illustrates oxygenated blood flowing into the left ventricle 208 during contraction of the left atrium 206 with the mitral valve 222 open, thereby allowing oxygenated blood 226 to flow into the left ventricle 208 which is expanding during this part of the cycle. The aortic valve 224 is closed at this instant. An intra-cardiac device including an atrial component 102 and a ventricular component 104 facilitates the flow of the oxygenated blood 226 by volumetric displacement. The atrial intra-cardiac device component (ICDC) 102 within the left atrium 206 expands (increases in volume) when the left atrium 206 is emptying/contracting. The ventricular ICDC 104 contracts (decreases in volume) when the left ventricle 208 is filling/relaxing. During the next part of the cycle, the expansion/contraction process is reversed, i.e., the left atrium 206 is expanding and left ventricle 208 is shrinking. In this next part of the cycle the aortic valve 224 would then be open, thereby allowing oxygenated blood 226 to flow to the body and the mitral valve 222 would be shut. Similar expansion/contraction occurs in the right atrium and right ventricle and with their respective valves. Thus, the ICDCs support the heart in both the filling and emptying phases by volumetric displacement of blood via expansion/contraction.

Figure 2:
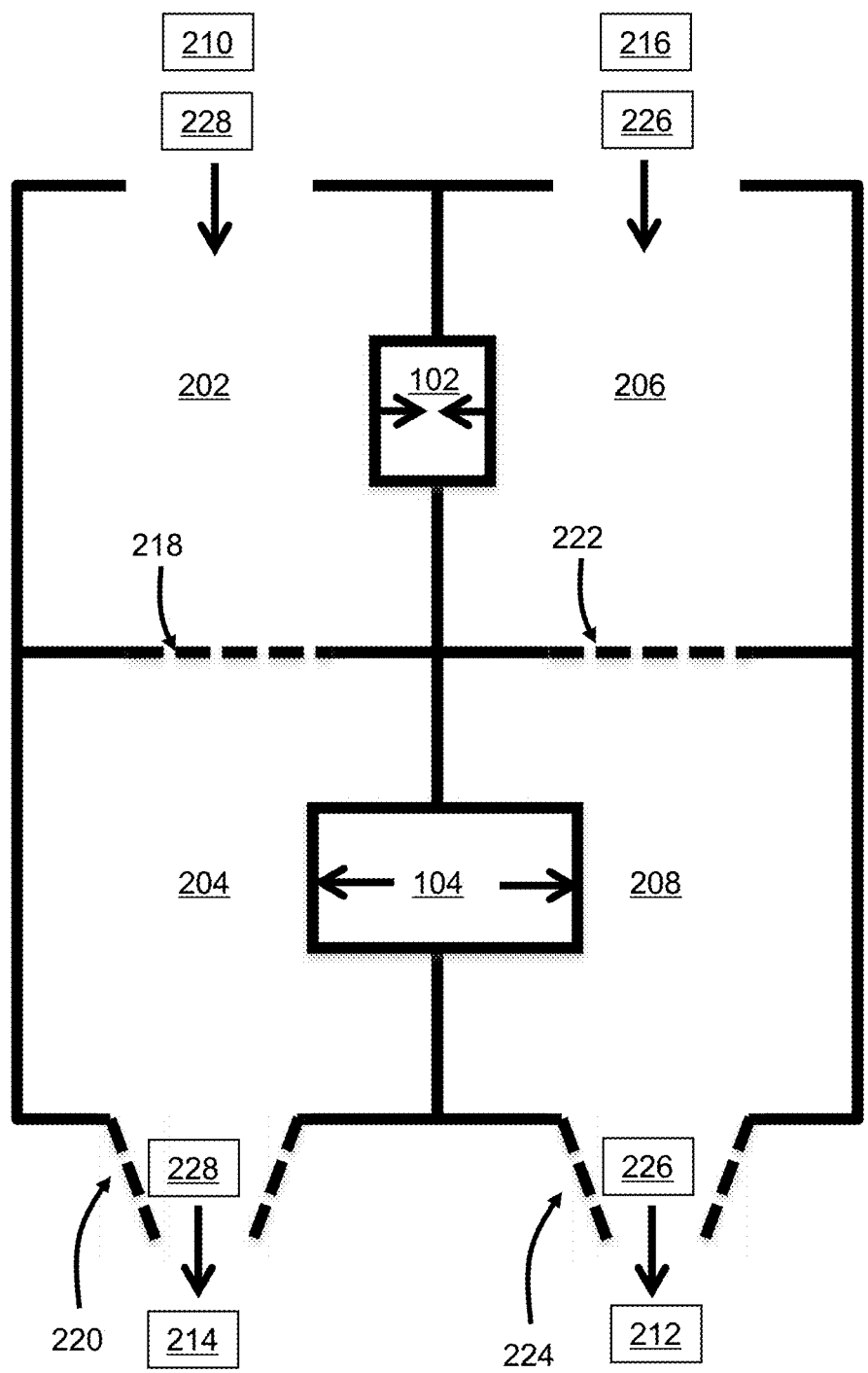
FIG. 2 illustrates the intra-cardiac device component functioning during blood ejection from ventricles.

FIG. 2 illustrates the ICDCs 102, 104 functioning during blood ejection from ventricles. The ventricular ICDC 104 expands when the right ventricle 204 and left ventricle 208 are emptying/contracting. The ventricular ICDC 104 is expanding in the right ventricle 204 pushing deoxygenated blood 228 through the pulmonary valve 220 into the pulmonary artery 214. Concurrently, the ventricular ICDC 104 is pushing oxygenated blood 226 from the left ventricle 208 through the aortic valve 224 into the aorta 212. The tricuspid valve 218 is closed. The mitral valve 222 is also closed. During this time, the atrial ICDC 102 shrinks, which helps deoxygenated blood 228 flow from the inferior vena cava and superior vena cava 210 into the relaxing right atrium 202 and oxygenated blood 226 flow from the pulmonary veins 216 into the relaxing left atrium 206. Not all chambers in the heart are the same size and shape so each ICDC may be specially designed for that chamber, e.g. with a specific volume displacement due to expansion and contraction.

Figure 3:
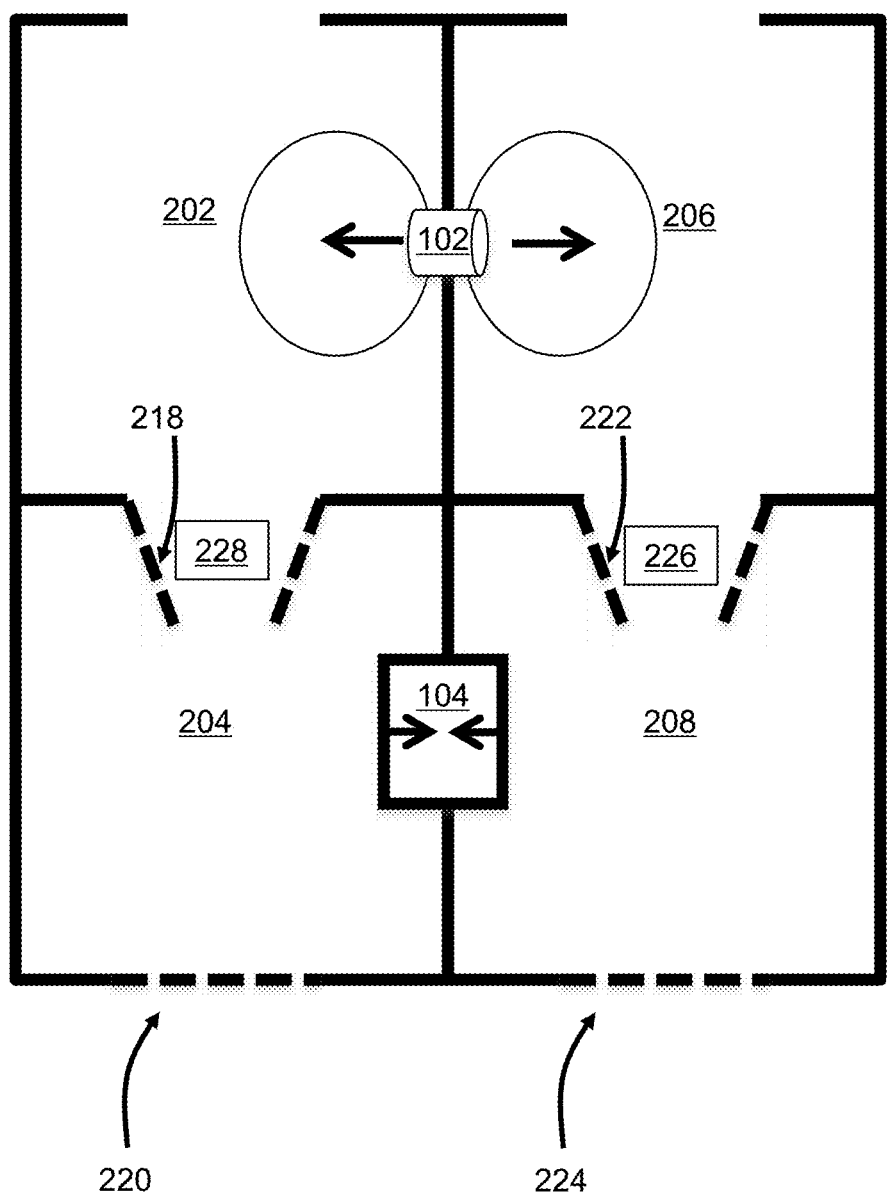
FIG. 3 illustrates the intra-cardiac device component functioning during blood ejection from atria.

FIG. 3 illustrates the ICDCs functioning during blood ejection from atria. This epoch of heart functioning follows the epoch described in FIG. 2. The atrial ICDC 102 expands when the right atrium 202 and left atrium 208 are emptying. The ventricular ICDC 104 shrinks when the right ventricle 204 and left ventricle 208 are filling. The ICDCs can be comprised of different materials, shapes and sizes. For illustrative purposes, the atrial ICDC 102 is shown with a balloon-type design and the ventricle ICDC 104 is shown with a piston-cylinder-type design. The tricuspid valve 218 is open allowing deoxygenated blood 228 to flow from the right atrium 202 to the right ventricle 204. The pulmonary valve 220 is closed. The mitral valve 222 is open so that oxygenated blood 226 can flow from the left atrium 206 to the left ventricle 208. The pulmonary valve 220 and aortic valve 224 are closed during this epoch.

Figure 4:
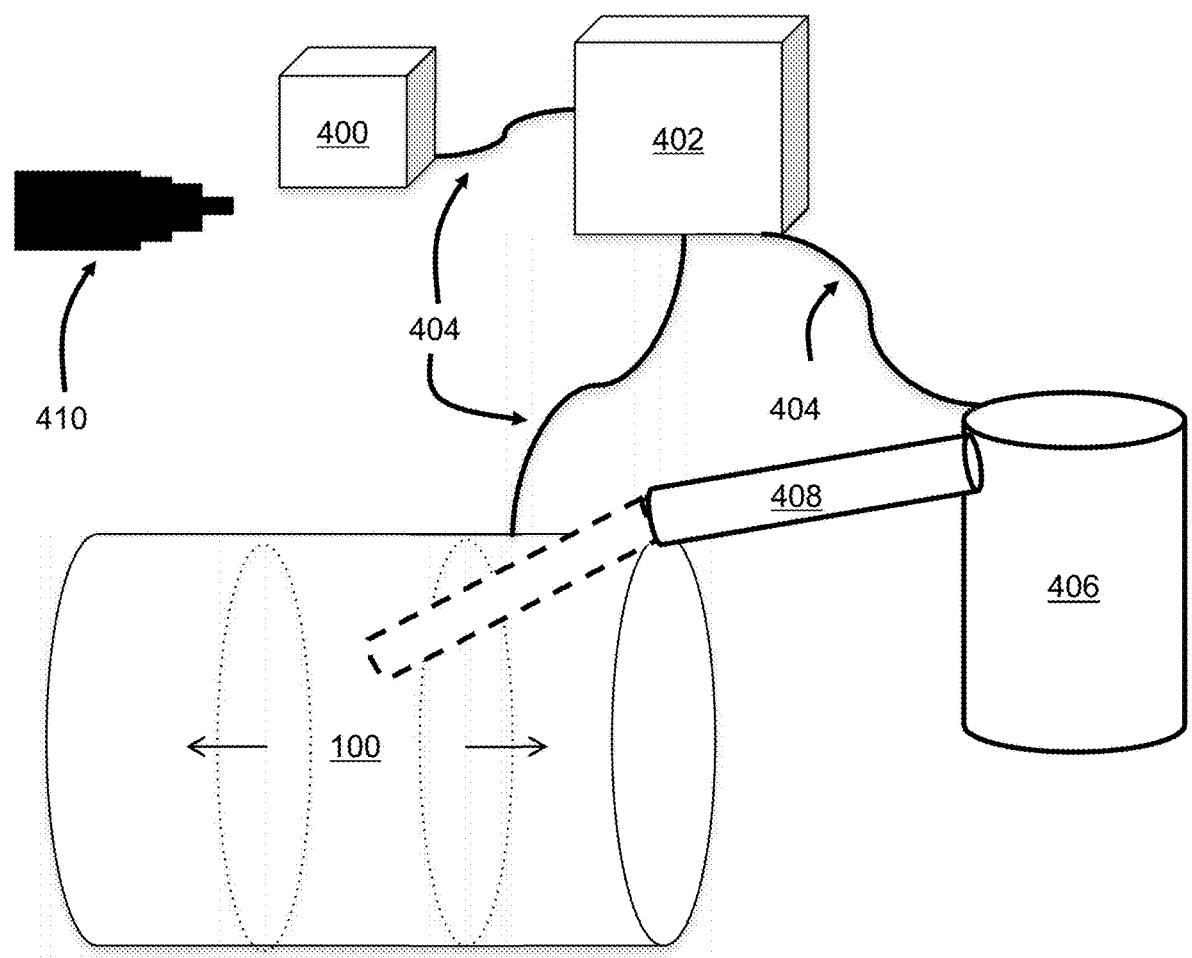
FIG. 4 illustrates an implementation of the intra-cardiac pump system components.

FIG. 4 illustrates an implementation of a piston-cylinder-type ICDC 100 in greater detail. A battery pack 400 provides power for the system. A computer/control system 402, which can be an intra-cardiac or external (e.g., subcutaneous chest wall) programmable device provides timing for the ICDC 100. These computer/control system 402 commands can be transmitted to the ICDC through the electrical connection 404 or via wireless system. The right portion of the figure shows a fluid storage device 406 (e.g., compressed air, non-compressible fluid). The fluid flows from the storage device to the ICDC 100 via tubing 408 (i.e., made of non-compliant materials). Also shown is a penetrator device 410, which is designed to perforate (i.e., create a small hole) the inter-atrial septum or the interventricular septum for device placement. Variations to this system layout include whether key components are internal or external to the body. Note that the ICDC 100 has multiple sub-elements that will be described below in FIG. 7, including: external casing sub-element; internal support structure; volume expansion/shrinkage sub-element; internal medium sub-element; heart fixation sub-element; sensor components; and, control components.

Figure 5:
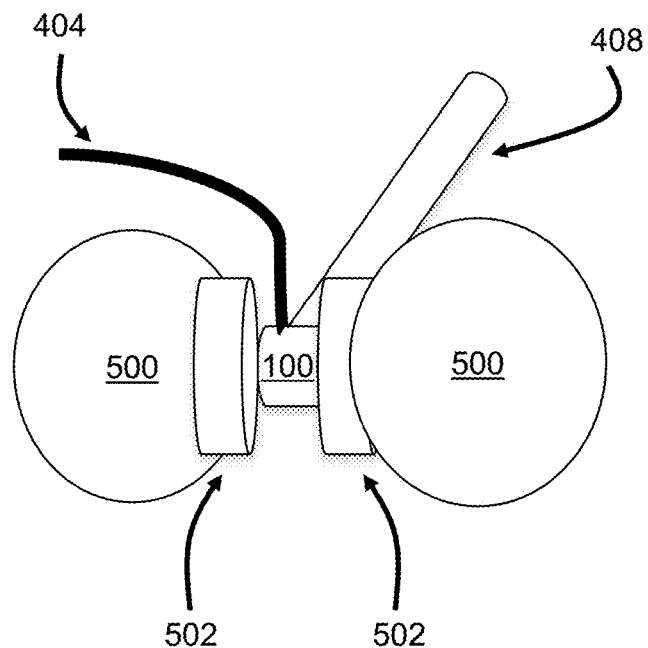
FIG. 5 illustrates the intra-cardiac device component (ICDC) sub-elements.

FIG. 5 illustrates sub-elements of a balloon-design-type ICDC in greater detail. The tubing for passage of fluids 408 (e.g., compressed air) joins the sub-component of the ICDC that traverses the interatrial septum or interventricular septum. Two balloons 500 are connected by the sub-components 502 of the ICDC that affixes to the interatrial septum or intraventricular septum. The balloon sub-components 500 of the ICDC expand and contract to displace blood to assist with heart pumping. These balloons 500 are located in either left and right atriums or left and right ventricles or both. As noted on the figure, although two balloons 500 are shown, the expansion/contraction sub-elements could include, but are not limited to, a cylinder with internal piston or similar device which would allow for expansion to push blood out of the chamber or contraction to allow flow of blood into the chamber. A balloon 500 volume expansion/contraction sub-element in right atrium/ventricle encloses internal medium sub-element. The ICDC can transmit or receive via the electrical connection 404 or wireless communication. A sub-component of the ICDC 100 would traverse through the wall separating the respective chambers (interatrial septum or interventricular septum). Heart fixation sub-elements 502 onto inter-atrial septum or inter-ventricular septum. External casing sub-element encloses internal support structure and houses sensor components and control components.

Figure 6:
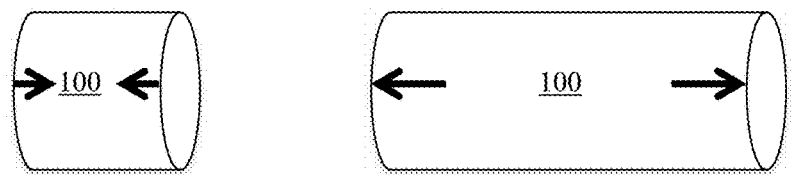
FIG. 6 illustrates the intra-cardiac device component volume during expansion/contraction phases and internal pressure.

FIG. 6 quantifies volumetric displacement by an ICDC 100 during expansion/contraction phases and internal pressure. Specifically, volumes and pressures within the ICDC are shown as a function of expansion (i.e., enlarging) and contraction (i.e., shrinking). The volumes and pressures shown are merely illustrative and would vary depending on the patient.

Figure 7:
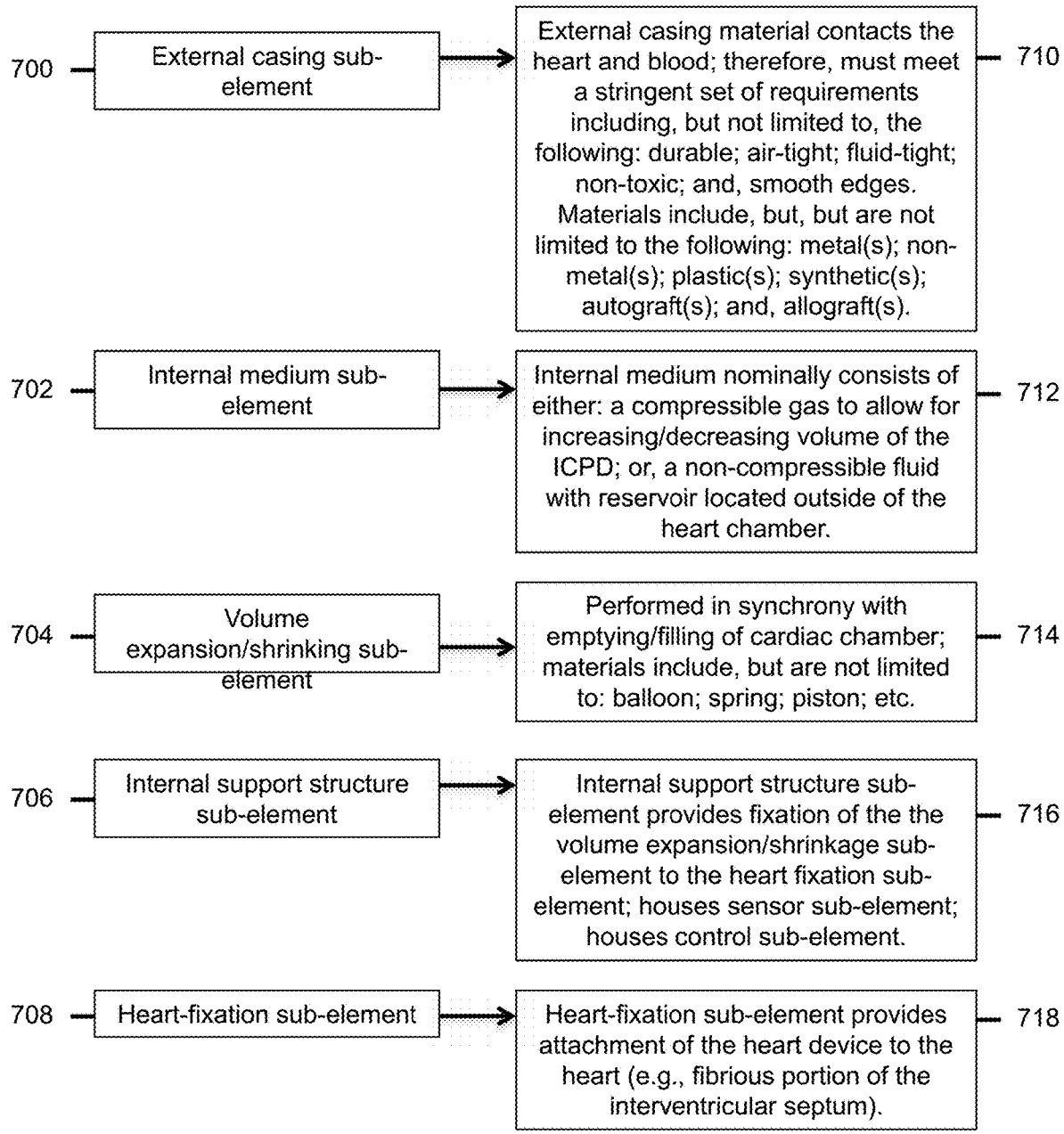
FIG. 7 illustrates the intra-cardiac device component requirements.

FIG. 7 illustrates ICDC functions and requirements. Although the figure is self-explanatory, it is important to note the design flexibility. For example, a wide range of non-toxic materials could be used for the ICDC. Similarly, different mechanisms could be used to displace volumes of blood via expansion/contraction or decompression/compression. There are multiple sub-elements of the ICDC including: an external casing sub-element 700; an internal medium sub-element 702; a volume expansion/shrinking sub-element 704; an internal support structure sub-element 706; and, a heart-fixation sub-element 708. The external casing sub-element 700 has specific design requirements 710. Since the external casing material contacts the heart and blood, it should meet a stringent set of requirements including, but not limited to, the following: durable; air-tight; fluid-tight; non-toxic; and, smooth edges. Materials may include but are not limited to the following: metal(s); non-metal(s); plastic(s); synthetic(s); autograft(s); and, allograft(s). The internal medium sub-element 702 may have specific design requirements 712. The internal medium nominally consists of either: a compressible gas to allow for increasing/decreasing volume of the ICDC; or, a non-compressible fluid with reservoir located outside of the heart chamber. The volume expansion/shrinking sub-element 704 has specific design requirements 714. The volume expansion/shrinking sub-element is performed in synchrony with emptying/filling of cardiac chamber. The materials may include, but are not limited to: balloon; spring; piston; etc. The internal support structure sub-element 706 may have specific design requirements 716. The internal support structure sub-element provides the following: fixation of the volume expansion/shrinkage sub-element to the heart fixation sub-element; houses sensor sub-element; and, houses control sub-element. The heart fixation sub-element 708 has specific design requirements 718. The heart-fixation sub-element provides attachment of the heart device to the heart (e.g., fibrous portion of the interventricular septum).

Figure 8:
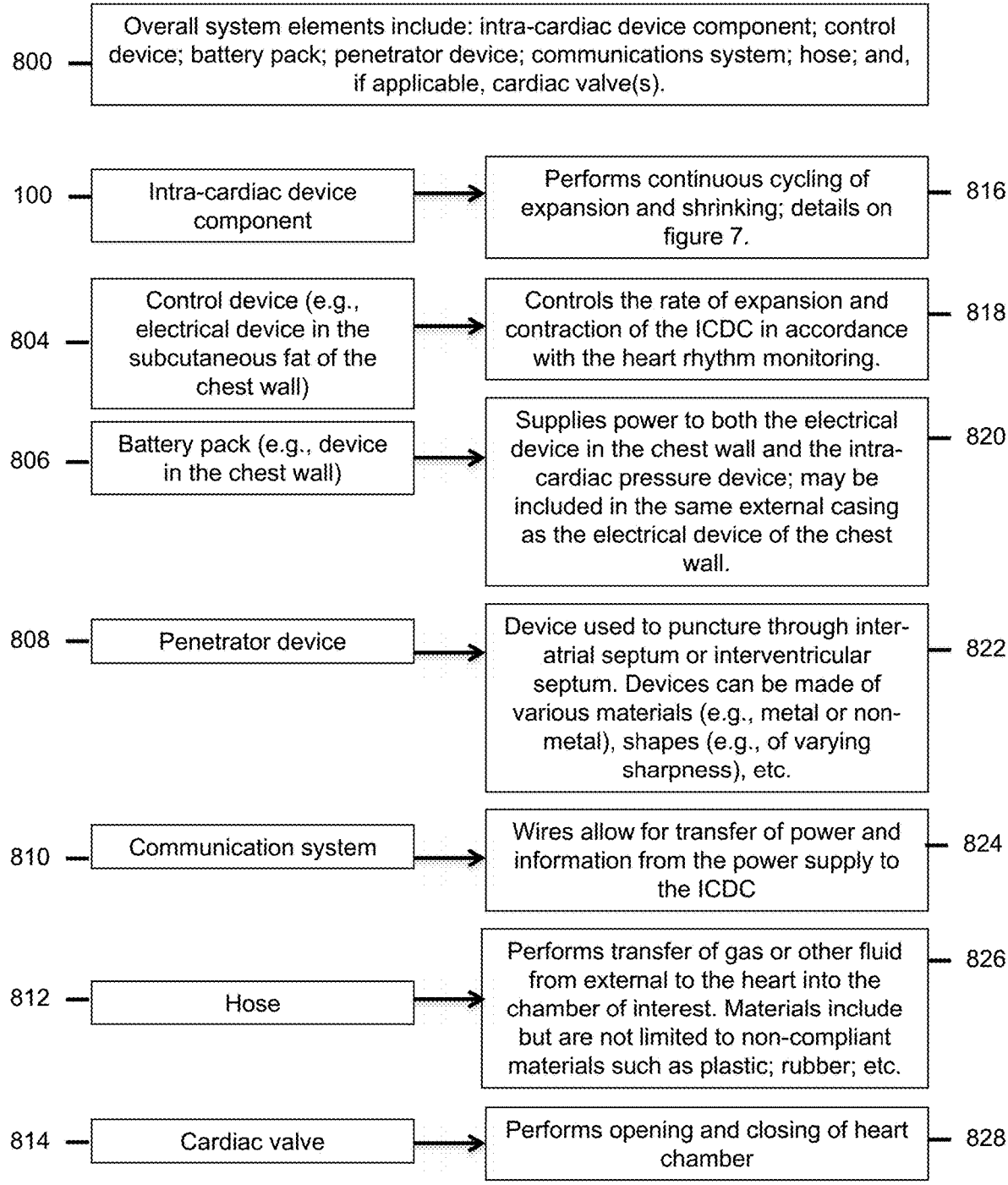
FIG. 8 illustrates overall intra-cardiac pump system components.

FIG. 8 illustrates overall system components. The overall system 800 has multiple elements: intra-cardiac device component 100; control device 804; battery pack 806; penetrator device 808; communications system 810; hose 812; and, if applicable, cardiac valve(s) 814. The ICDC 100 function 816 is to perform continuous cycling of shrinking and expansion 816. The control device 804 (e.g., electrical device in the subcutaneous fat of the chest wall) function 818 is to control the ICDC parameters (e.g., rate and volume of expansion/contraction, etc.) in accordance with the heart rhythm monitoring. The battery back 806 (e.g., battery is included in the casing of the device in the subcutaneous fat of the chest wall) function 806 is to supply power to both the electrical device in the chest wall and the ICDC 820. The battery pack may be included in the same external casing as the electrical device of the chest wall or separate for easier exchange. The penetrator device 808 function 822 is to puncture through the inter-atrial septum or inter-ventricular septum. The penetrator device 808 can be made of various materials (e.g., metal or non-metal), shapes (e.g., of varying sharpness), etc. The penetrator device 808 may be single use only at the time of placement of the ICDC. The communication system 810 function 824 is to provide transfer of power and information amongst elements of the intra-cardiac pump overall system. Note that a wireless communications system 810 may also be implemented. The hose sub-element 812 has the function 826 of performing transfer of gas or other fluid to allow the ICDC to expand or contract. Note that the gas or fluid can be transferred from outside to the heart to inside the heart during the expansion phase of the ICDC. Alternatively, the gas or fluid can be transferred from the ICDC component in one chamber to the ICDC component in another chamber. The hose 812 can be made of materials including, but not limited to, noncompliant materials including plastic, rubber, Gore-Tex®, etc. Additionally, it is possible to integrate cardiac valve(s) 814 into this overall system, such that the ICDC 100 works in conjunction with the cardiac valve 814 function 828 of cycles of openings and closings.

Figure 9:
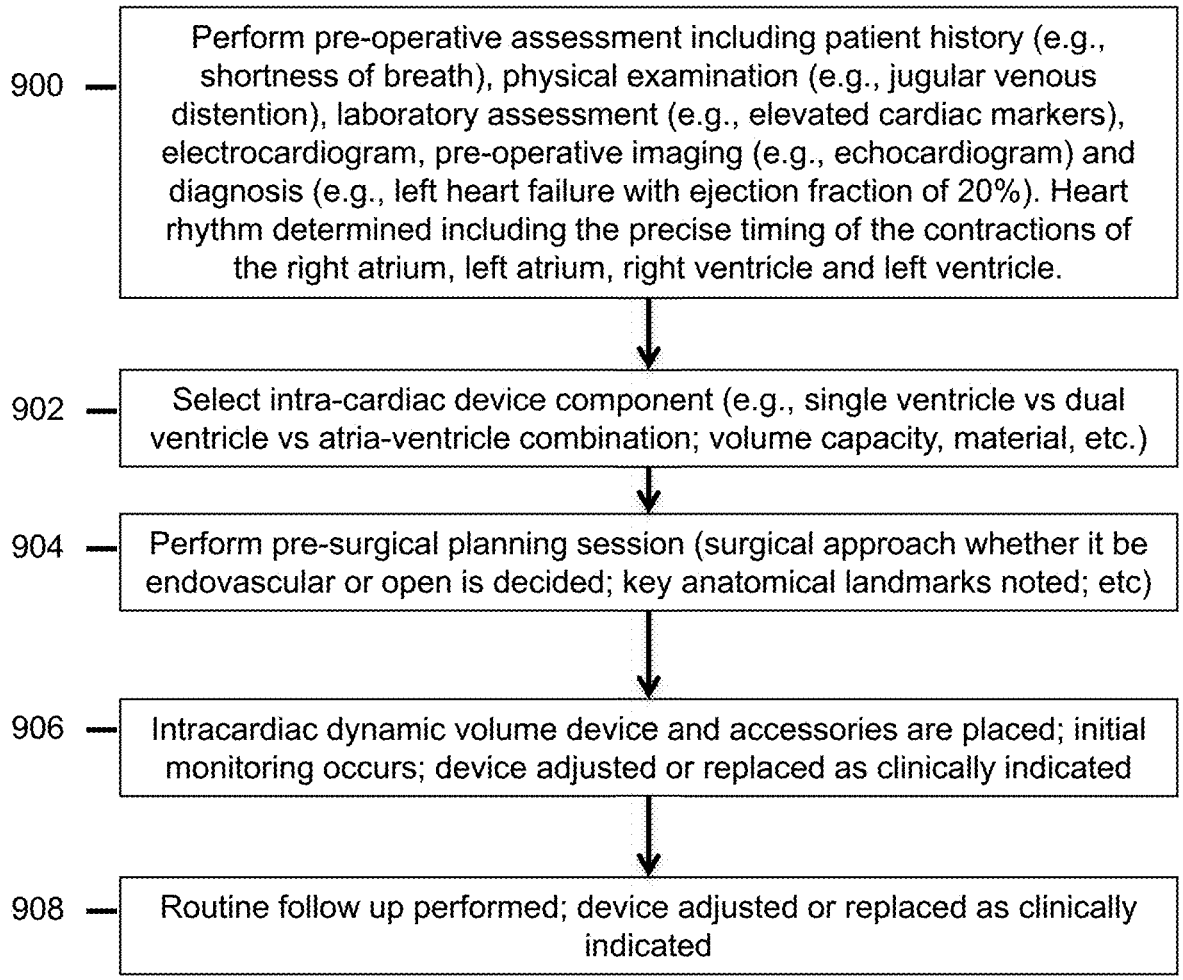
FIG. 9 illustrates an overview of the clinical setting, placement of the device and the follow up period.

FIG. 9 illustrates an overview of the clinical setting, placement of the device and the follow up period. This figure places in context the process under which the patient would be treated. Of importance is the pre-planning that must be done regarding internal placement of ICDCs. Note also there is considerable flexibility in the number of expansion/contraction devices emplaced in the heart which could range from one chamber to all four chambers. Note also that during the period closely following the emplacement of the intra-cardiac device components, there is a clinical review and adjustments made to the timing and volumetric expansion/contraction as required. The first step 900 is to perform pre-operative assessment including patient history (e.g., shortness of breath), physical examination (e.g., jugular venous distention), laboratory assessment (e.g., elevated cardiac markers), pre-operative imaging (e.g., echocardiogram) and diagnosis (e.g., left heart failure with ejection fraction of 20%). The heart rhythm and precise timing of the contractions of the right atrium, left atrium, right ventricle and left ventricle is precisely characterized. The second step 902 is to select the specific intra-cardiac device component (e.g., single ventricle vs dual ventricle vs atria-ventricle combination; volume capacity, material, etc.) as well as the supporting equipment as described in FIG. 8. The third step 904 is to perform pre-surgical planning session(s) (e.g., determine whether it be endovascular or open procedure; key anatomical landmarks noted; etc.). The fourth step 906 is the placement of the ICDC and accessories. Also, the staff will perform initial monitoring, adjust the device (or replaced as clinically indicated), etc. The fifth, and final, step 908 is to perform routine follow up wherein the device adjusted or replaced as clinically indicated.

Figure 10:
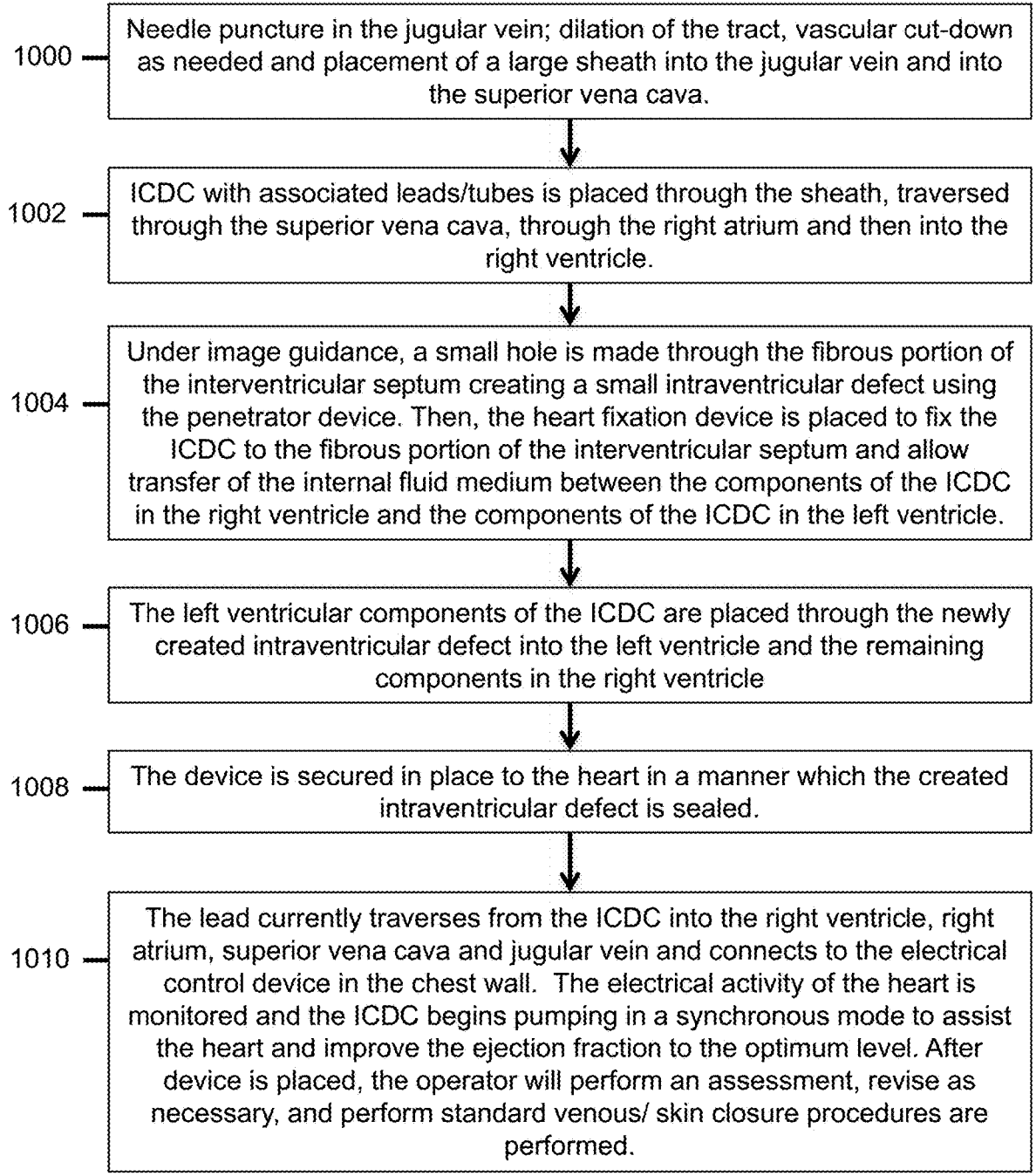
FIG. 10 illustrates an overview of the preferred method of placement of the ICDC.

FIG. 10 illustrates an overview of a method of placement of the ICDC endovascularly through the venous side with the preferred venous access site being the jugular vein. The first step 1000 is a needle puncture in the jugular vein, dilation of the tract, vascular cut-down as needed and placement of a large sheath into the jugular vein and then into the superior vena cava. There are multiple paths by which the intra-cardiac device expansion/contraction component(s) can be place into the heart. Alternatively, this could be placed through femoral vein access. The second step 1002 is placing the ICDC with associated leads/tubes through the sheath, traversing through the superior vena cava, through the right atrium and then into the right ventricle. The third step 1004 is under image guidance, a small hole is made through the fibrous portion of the interventricular septum creating a small interventricular defect using the penetrator device. Then, the heart fixation device is placed to fix the ICDC to the fibrous portion of the interventricular septum and allow transfer of the internal fluid medium between the components of the ICDC in the right ventricle and the components of the ICDC in the left ventricle. The fourth step 1006 is for the left ventricular components of the ICDC to be placed through the newly created interventricular defect into the left ventricle and the right ventricular components of the ICDC in the right ventricle. The fifth step 1008 is for the device to be secured in place to the heart in a manner which the created intraventricular defect is sealed. The sixth step 1010 is to place that lead such that it traverses from the ICDC into the right ventricle, right atrium, superior vena cava and jugular vein and connects to the electrical control device in the chest wall. The electrical activity of the heart is monitored and the ICDC begins pumping in a synchronous mode to assist the heart and improve the ejection fraction to the optimum level. After device is placed, the operator will perform an assessment, revise as necessary, and perform standard venous/skin closure procedures are performed.

Figure 11:
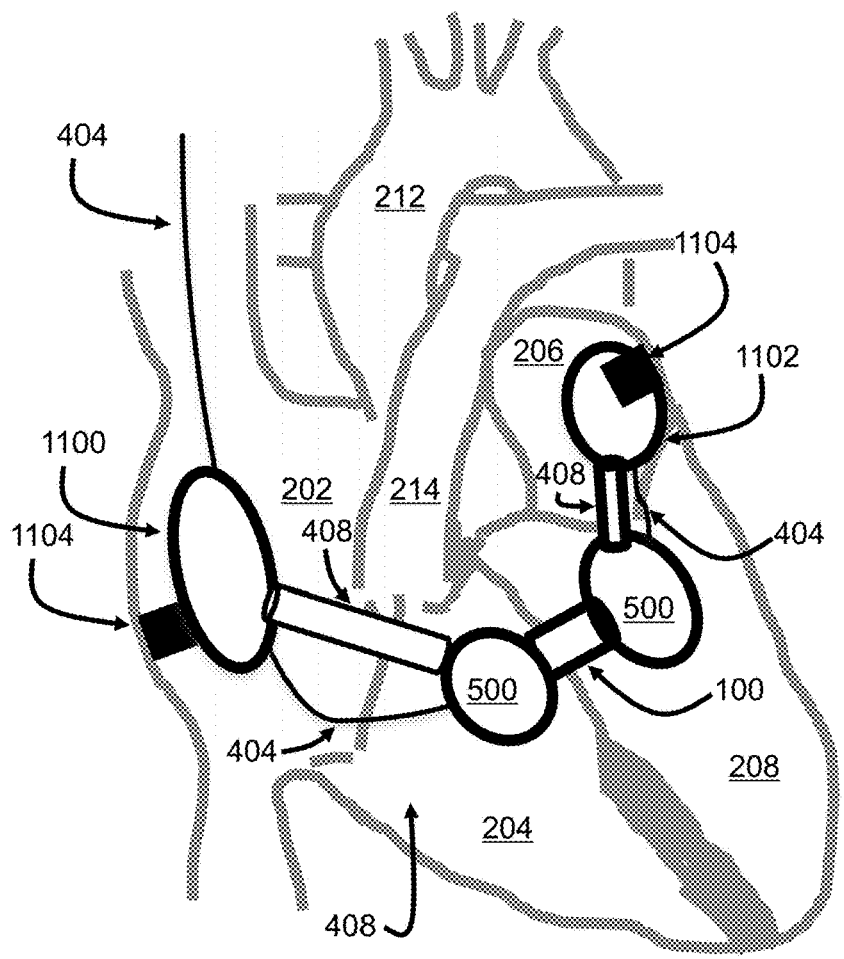
FIG. 11 illustrates the heart and arteries with respective pressures during expansion and contraction.

FIG. 11 illustrates the heart and arteries with respective pressures during expansion and contraction. A wire 404 is shown passing from the superior vena cava into the right atrium 202 through the tricuspid valve 204 and to the ICDC device 100 positioned at the fibrous portion of the interventricular septum with a balloon component 500 located in the right ventricle 204 and left ventricle 208. Also shown is a table illustrating the goal pressures in the heart chambers and exiting arteries. Note the near order of magnitude differences in pressures between left ventricle (LV)/aorta and other chambers in the heart. This higher pressure is obtained by the strong muscular structure of the left ventricle 208. Also note that when a patient has a myocardial infarction, some of this muscular tissue may be damaged resulting in a loss of the cardiac output. This loss is compensated by the expansion/contraction element 500 of the ICDC 100. This may help the left ventricle recover function over time. The volumes of the expansion/compression elements 500 located in left ventricle 208 and right ventricle 204 can be the same or vary slightly different as desired by the physician. This illustrates that the specific sizes of these elements will be determined based on the specific heart structure and condition of the patient at hand. An alternative setup would be to have a single fluid storage source 1100 located in the right atrium 202. Another alternative setup would be to have a fluid storage source 1100 located in the right atrium and a fluid storage source located in the left atrium 1102. The fluid storage sources could be affixed to the atria by securing devices 1104. This setup would allow endovascular placement of all structures connected in a single device since all structures are connected in a linear fashion.

Figure 12:
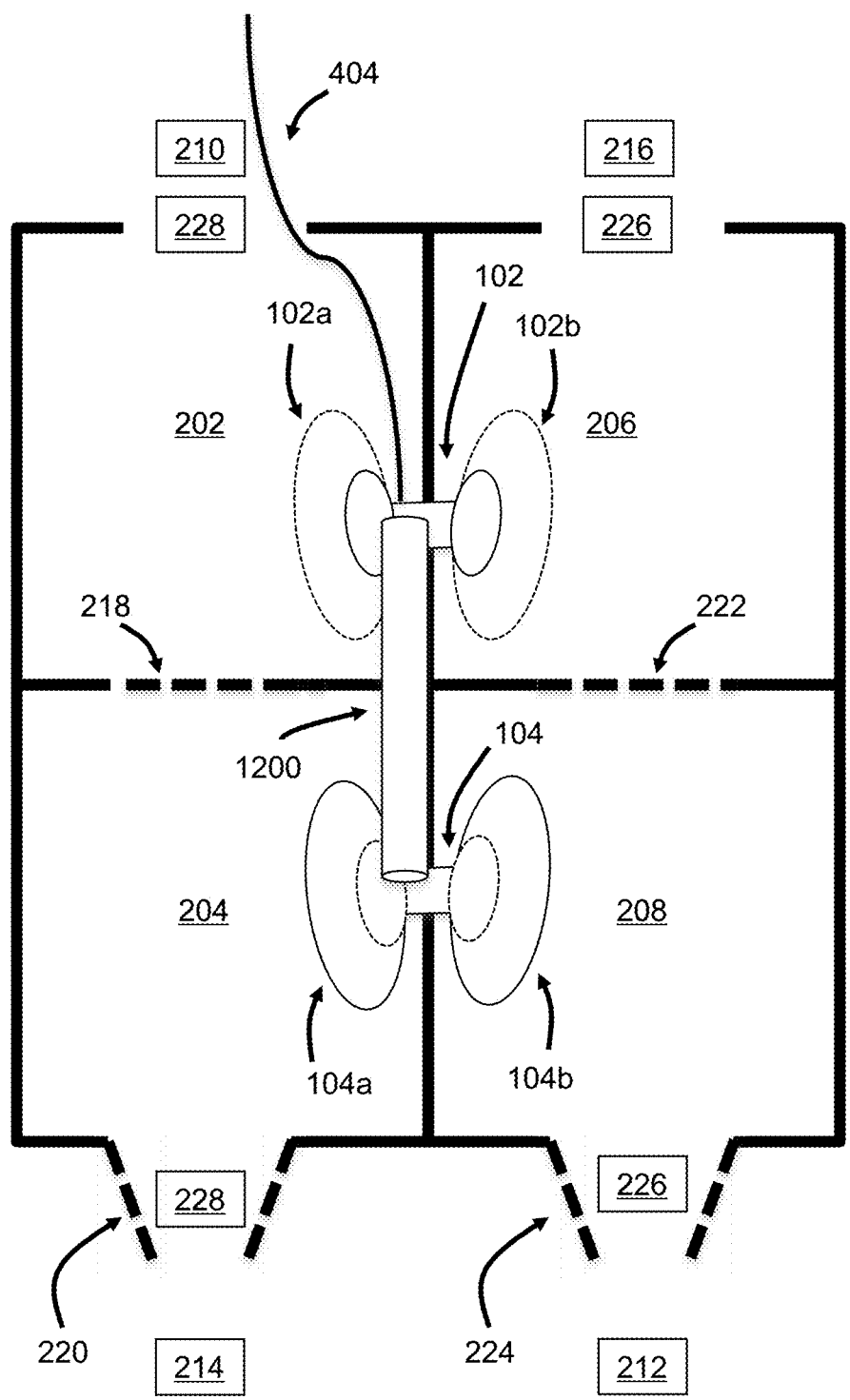
FIG. 12 illustrates a system wherein some of the fluid is shifted back and forth from the atrial components of the ICDC to the ventricular components of the ICDC.

FIG. 12 illustrates a system wherein some of the fluid is shifted back and forth from the atrial ICDC 102 to the ventricle ICDC 104. This illustration is in the time epoch wherein the left ventricle 208 is ejecting oxygenated blood 226 into the aorta 212. A right atrial displacement sub-component 102a of ICDC 102 shrinks (illustrated moving from large dashed line ellipse to smaller solid line ellipse), which helps pull deoxygenated blood 228 from the superior vena cava/inferior vena cava 210 into the right atrium 202. A left atrial displacement sub-component 102b of ICDC 102 shrinks (illustrated moving from large dashed line ellipse to smaller solid line ellipse), which helps pull oxygenated blood 226 from the pulmonary veins 216 into the left atrium 206. A right ventricular displacement sub-component 104a of the ICDC 104 expands (illustrated moving from dashed line ellipse to larger solid line ellipse), which helps the right ventricle 204 to eject deoxygenated blood 228 through the open pulmonic valve 220 into the pulmonary artery 214. Note that the tricuspid valve 218 is closed during this time epoch. A left ventricular displacement sub-component 104b of the ICDC 104 expands (illustrated moving from dashed line ellipse to larger solid line ellipse), which helps the left ventricle 208 to eject oxygenated blood 226 through the open aortic valve 224 into the aorta 212. Note that the mitral valve 222 is closed during this time epoch. As the atrial displacement components of the ICDC 102 shrink, the fluid medium travels from the atrial displacement components of the ICDC to the hose 1200. The location of the hose 1200 can vary (e.g., course through any combination of the right atrium 202, right ventricle 204, left atrium 206, left ventricle 208, valves or myocardium). Also shown is the wire 404 connecting the ICDC to the rest of the apparatus. Note that the balloon size, shape, material and other properties can be altered such that it is optimally designed for the cardiac chamber that it is placed in. The epoch illustrated in the figure has blood filling the atria and blood exiting the ventricles. This particular configuration stores the fluid within the intra-cardiac device expansion/contraction components shown and obviates the need for a fluid storage device (e.g., stored outside the heart such as in the pleural space) and associated tubing from the fluid storage device. A sub-element within the cylinder connecting the intra-cardiac device expansion/contraction components within the atriums and those within the ventricles could have a piston (or other type of sub-element) that pulls fluid from the atrium intra-cardiac device expansion/contraction components and pushes the fluid into the ventricle intra-cardiac device expansion/contraction components. This process would be reversed during the following epoch of heart functioning.

Figure 13:
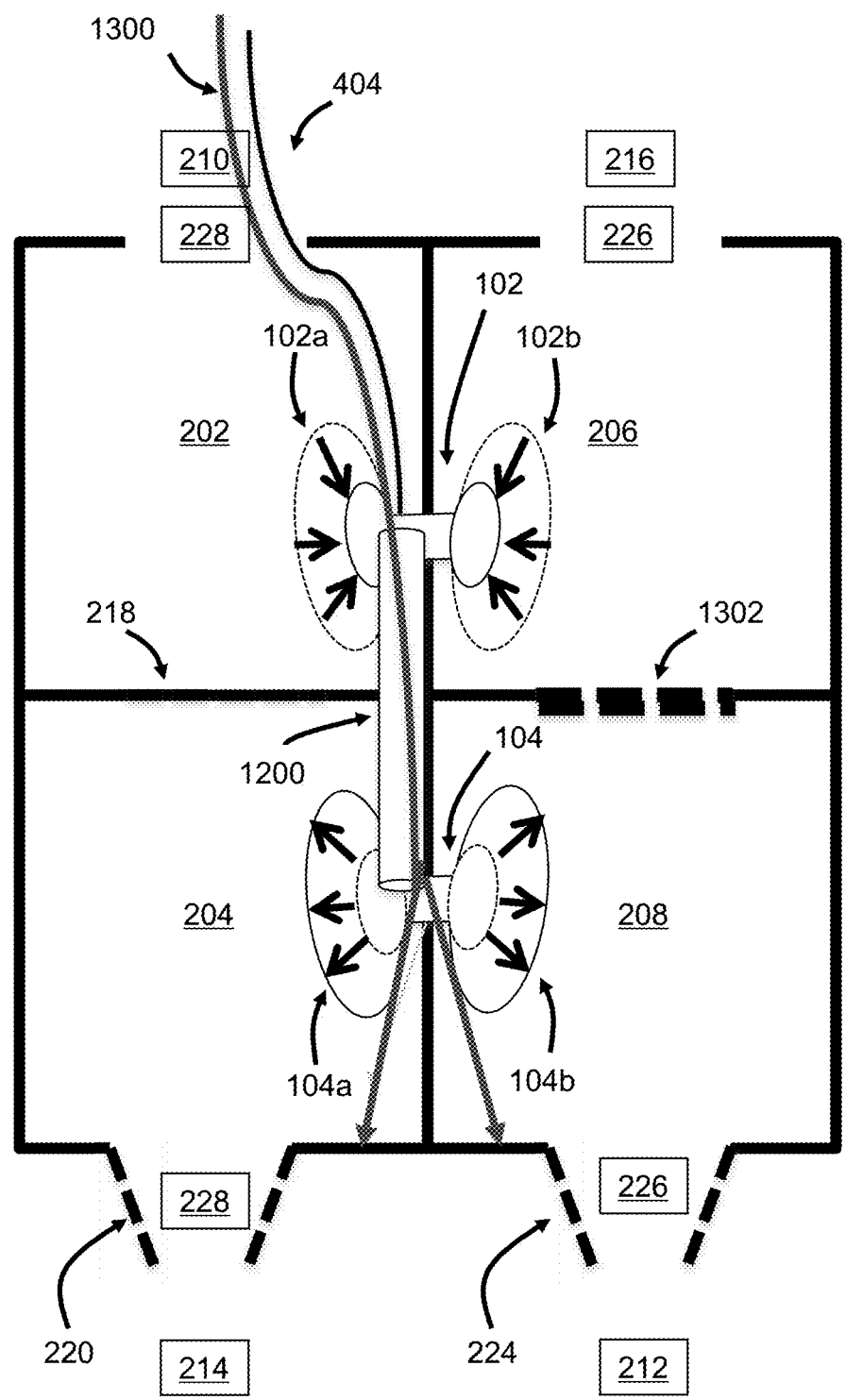
FIG. 13 illustrates an ICDC system with the addition of electrodes to stimulate heart function and an artificial valve.

FIG. 13 illustrates an ICDC system with the addition of electrodes to stimulate heart function and an artificial valve. This illustration is in the time epoch wherein the left ventricle 208 is ejecting oxygenated blood 226 into the aorta 212. The right atrial displacement sub-component 102a of the ICDC 102 shrinks (illustrated moving from large dashed line ellipse to smaller solid line ellipse), which helps pull deoxygenated blood 228 from the superior vena cava/inferior vena cava 210 into the right atrium 202. The left atrial displacement sub-component 102b of the ICDC 102 shrinks (illustrated moving from large dashed line ellipse to smaller solid line ellipse), which helps pull oxygenated blood 226 from the pulmonary veins 216 into the left atrium 206. The right ventricular displacement sub-component 104a of the ICDC 104 expands (illustrated moving from dashed line ellipse to larger solid line ellipse), which helps the right ventricle 204 to eject deoxygenated blood 228 through the open pulmonic valve into the pulmonary artery 214. Note that the tricuspid valve 218 is closed during this time epoch. The left ventricular displacement sub-component 104b of the ICDC 104 expands (illustrated moving from dashed line ellipse to larger solid line ellipse), which helps the left ventricle 208 to eject oxygenated blood 226 through the open aortic valve 224 into the aorta 212. Note that the mitral valve 222 is closed during this time epoch. As the atrial displacement components of the ICDC 102 shrink, the fluid medium travels from the atrial displacement components of the ICDC to the hose 1200. The location of the hose 1200 can vary (e.g., course through any combination of the right atrium 202, right ventricle 204, left atrium 206, left ventricle 208, valves or myocardium). Also shown is the wire 404 connecting the ICDC to the rest of the apparatus. A possible design alternative is to incorporate electrodes to stimulate the functioning of the heart. The electrodes and associated electrical connection wiring 1300 to transmit electrical pulses is shown in red and can be used to stimulate the right atrium 202, left atrium 206, right ventricle 204, left ventricle 208 or any combination thereof. The control component (not shown) would determine timing for transmitting the electrical pulses. These pulses would, in turn, signal contraction/relaxation of the chambers with corresponding valve opening/closing. Note also that artificial valves or other devices could also be incorporated into this overall apparatus. For example, an illustration of a mechanical mitral valve 1302 is shown.

Figure 14:
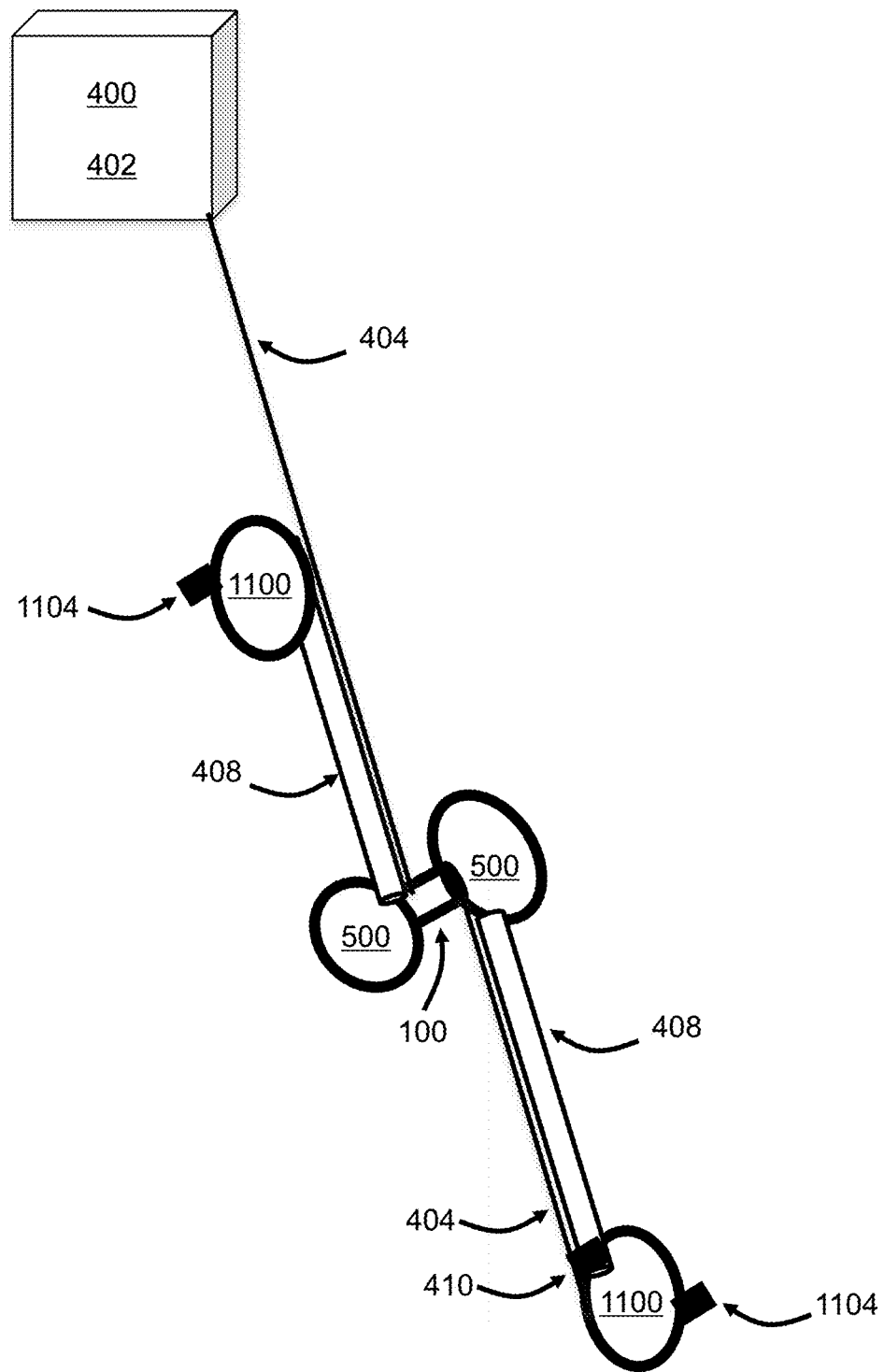
FIG. 14 illustrates the device which could be placed through a single puncture through the interventricular septum and yield intracardiac pumps into each atrium and each ventricle.

FIG. 14 illustrates an implementation that could be placed endovascularly through a single puncture through the interventricular septum and yield ICDCs into each atrium and each ventricle. The electrical control device 402 and battery 400 are connected to the ICDCs via a wire 404. The wire 404 is attached to the right atrial ICDC fluid storage device 1100, which is illustrated with a securing device 1104 such that it can be secured to the right atrium. Both a wire 404 and a fluid transport tube 408 extend from the right atrial ICDC fluid storage device 1100 to the right ventricular ICDC device 500. A fixation device 100 which has been placed through the interventricular septum connects the right ventricular ICDC device 500 to the left ventricular ICDC device 500. The fixation device 100 contains the wire 404 and, optionally, a tube. The wire 404 and tube 408 extend from the left ventricular ICDC device 500 to the reservoir 1100 in the left atrium, where it can be attached to the left atrium via a fixation device 1104. Near the end of the tube, a penetrator device 410 can be included such that the device can be placed through the interventricular septum. Alternatively, the penetrating device 410 can be a separate piece of equipment.

Figure 15:
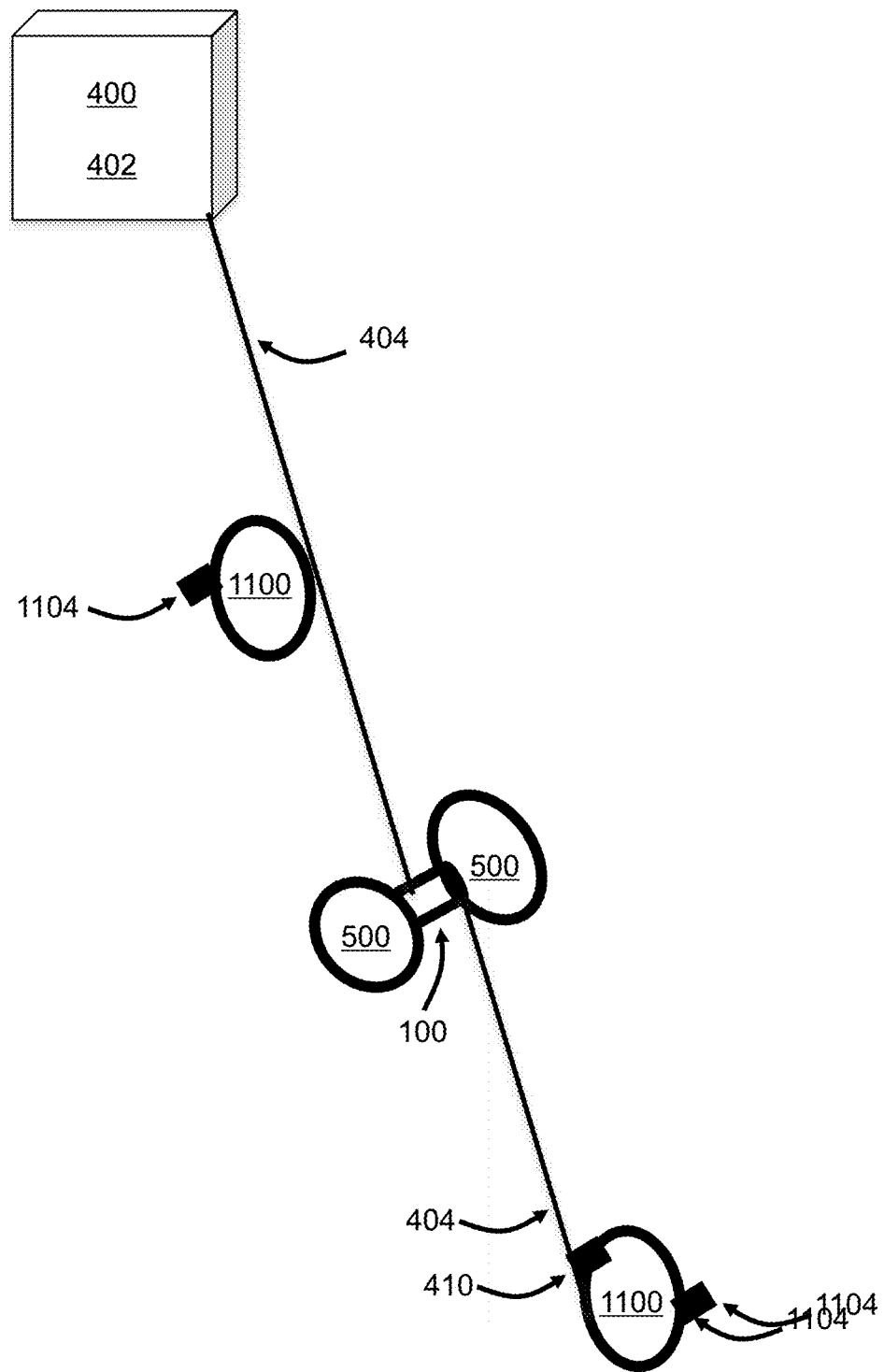
FIG. 15 illustrates an implementation that could be placed through a single puncture through the interventricular septum and yield ICDCs into each atrium and each ventricle.

FIG. 15 illustrates an implementation that could be placed through a single puncture through the interventricular septum and yield ICDCs into each atrium and each ventricle. The electrical control device 402 and battery 400 are connected to the ICDCs via a wire 404. The wire 404 is attached to the right atrial ICDC fluid storage device 1100, which is illustrated with a securing device 1104 such that it can be secured to the right atrium. A wire 404 extends from the right atrial ICDC fluid storage device 1100 to the right ventricular ICDC device 500. A fixation device 100 which has been placed through the interventricular septum connects the right ventricular ICDC device 500 to the left ventricular ICDC device 500. The fixation device 100 contains the wire 404. The wire 404 extends from the left ventricular ICDC device 500 to the reservoir in the left atrium. Near the end of the tube, a penetrator device 410 can be included such that the device can be placed through the interventricular septum. Alternatively, the penetrating device 410 can be a separate piece of equipment. Note that a tube is not present in this apparatus. A tubeless system can therefore be accomplished.

Figure 16:
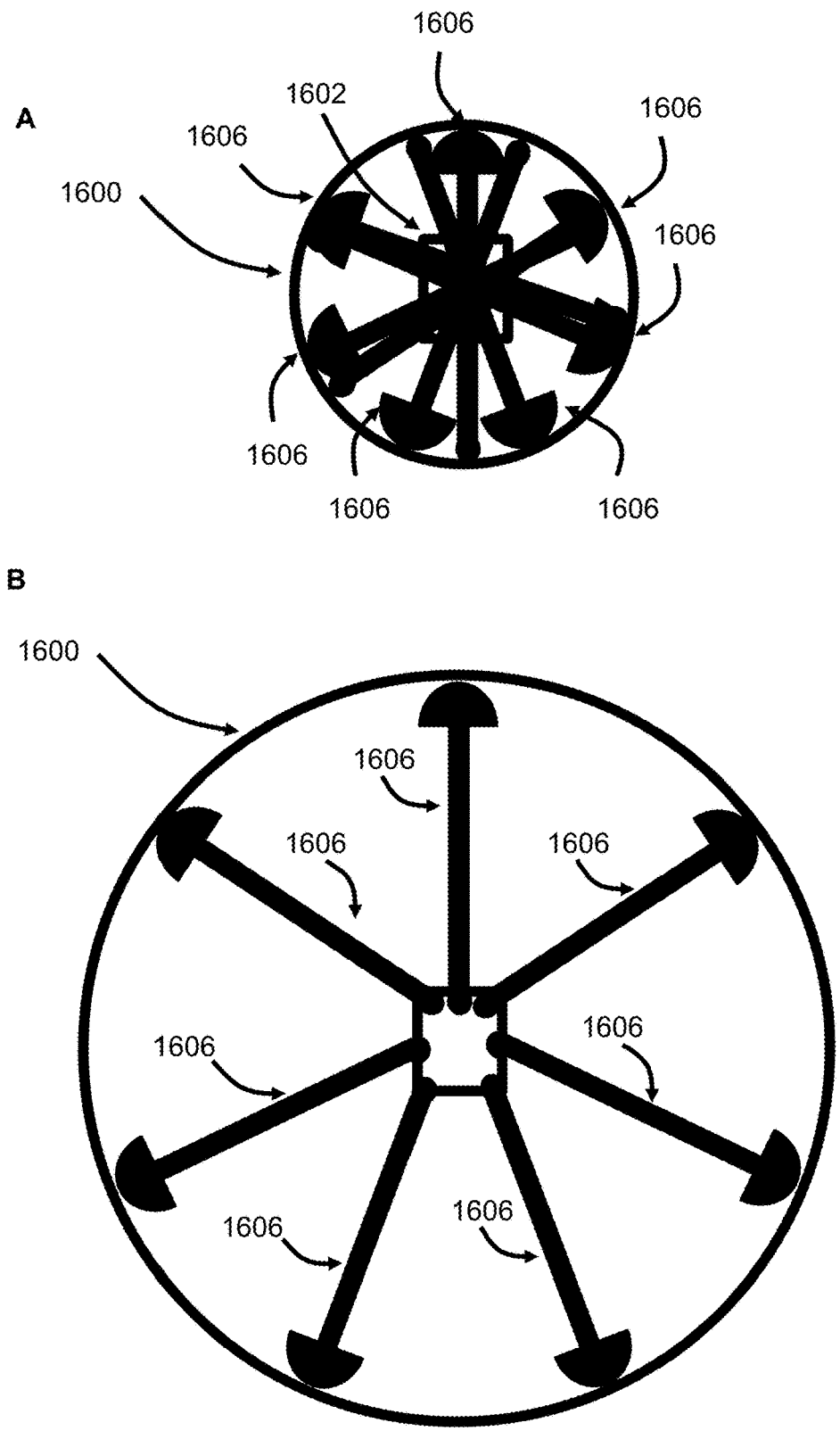
FIG. 16 illustrates an example ICDC device wherein the pressure inside the device decreases while the ICDC is expanding.

FIG. 16 illustrates an example ICDC device wherein the pressure inside the device decreases while the ICDC is expanding. This can be accomplished an air and apparatus filled balloon 1600 with a mechanical volumetric displacement device comprising a hub 1602 and spoke 1606 apparatus using pistons to alter the radius of the device and drive expansion and contraction of the device. FIG. 16A illustrates the contraction of the balloon 1600 wherein the radius of a spokes 1606 is decreased. During this time epoch, the pressure inside of the balloon increases and the pressure inside of the cardiac chamber decreases helping with cardiac chamber filling. FIG. 16B illustrates the expansion of the balloon 1600 through increasing the radius of the spokes 1606. During this time epoch, the pressure inside of the balloon drops and the pressure inside of the cardiac chamber increases helping with cardiac chamber emptying. The central hub of the ICDC would have pistons on spokes, which would project radially outward in a sphere-like shape. The tip of the spoke 1600 would contact the surface of the balloon 1600 and would be designed to be round and durable.

FIG. 17 quantifies the volumetric displacement by an ICDC during expansion/contraction phases and internal pressure. In this example, the difference in the volume of the ICDC from the expanded phase (volume of 34 mL) to the shrunken phase (volume of 4 mL) would be approximately 30 mL. The volume of compressible material (i.e., air) within material would be 33 mL in the expanded phase and 3 mL in the shrunken phase. The volume of non-compressible material within the ICDC is shown as 1 mL for both the expanded phase and the shrunken phase. Standard pressure-volume relationship calculations would be utilized. This illustrates that the ICDC pressure would be low in the expanded phase and higher in the shrunken phase. This system using air would obviate the need for multiple fluid storage devices.

Figure 18:
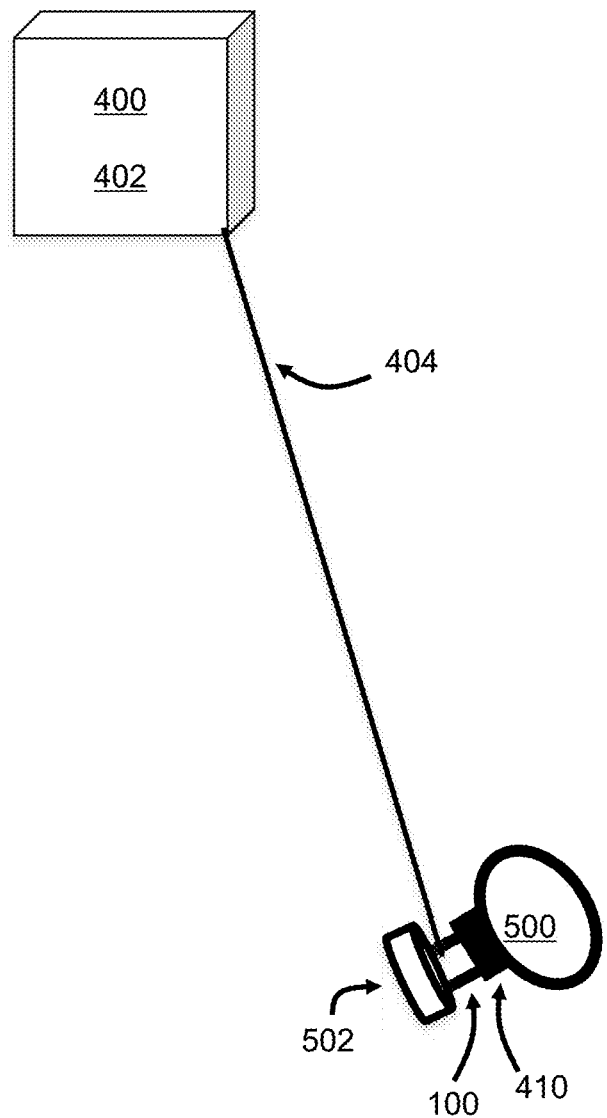
FIG. 18 illustrates a simplified system containing only a left ventricular ICDC without a reservoir.

FIG. 18 illustrates a simplified system containing only a left ventricular ICDC without a reservoir. This could be placed through a single puncture through the interventricular septum and yield a single ICDC into the left ventricle. The electrical control device 402 and battery 400 are connected to the ICDC via a wire 404. A portion of the ICDC 502 is used to secure the device to the right ventricular side of the interventricular septum, which is connected to another portion of the ICDC 100 traversing the interventricular septum and connecting to the left ventricular ICDC balloon device 500, which is shown in greater detail in FIG. 16. The fixation device 100 contains the wire 404. The wire 404 extends into the left ventricular ICDC device 500 to the reservoir in the left atrium. A penetrator device 410 can be included such that the device can be placed through the interventricular septum. Alternatively, the penetrating device 410 can be a separate piece of equipment. Note that both a tube and reservoir are not present in this apparatus, which highlights the flexibility of this system.

What is claimed is:

1. A method for treating a heart to increase blood flow, comprising the steps of:
    during a first epoch in which atrioventricular valves are closed and aortic and pulmonary valves are open, volumetrically contracting a balloon enclosed within an atrium and volumetrically expanding a balloon enclosed within a ventricle; and
    during a second epoch in which the atrioventricular valves are open and the aortic and pulmonary valves are closed, volumetrically expanding the balloon enclosed within the atrium and volumetrically contracting the balloon enclosed within the ventricle.

2. The method of claim 1 further comprising iterating volumetric expansion and volumetric contraction of the balloon enclosed within the atrium and the balloon enclosed within the ventricle in successive epochs in synchronization with sensed timing of the heart.

3. The method of claim 1 further comprising iterating volumetric expansion and volumetric contraction of the balloon enclosed within the atrium and the balloon enclosed within the ventricle in successive epochs in synchronization with a pacemaker.

4. The method of claim 1 further comprising iterating volumetric expansion and volumetric contraction of the balloon enclosed within the atrium and the balloon enclosed within the ventricle in successive epochs in response to input from a controller.

5. The method of claim 1 further comprising iterating volumetric expansion and volumetric contraction of the balloon enclosed within the atrium and the balloon enclosed within the ventricle in successive epochs in response to patient activity level.

6. The method of claim 1 further comprising calculating a first volume of expansion of the balloon enclosed within the atrium and calculating a second volume of expansion of the balloon enclosed within the ventricle, the first volume of expansion and the second volume of expansion calculated based on at least one of pre-existing blood ejection fraction for each chamber, size of each chamber; and desired output.

7. The method of claim 6 further comprising configuring the balloon enclosed within the atrium for the calculated first volume of expansion and the balloon enclosed within the ventricle for the calculated second volume of expansion.

8. The method of claim 6 further comprising adjusting the calculated first volume of expansion and adjusting the calculated second volume of expansion based on echocardiogram data.

9. The method of claim 6 further comprising storing data indicative of at least one of: the calculated first volume of expansion, the calculated second volume of expansion, associated volumes of blood ejected from each chamber for each epoch, number of epochs, total volume of blood pumped, and pressure in each chamber.

10. An apparatus comprising:
a balloon adapted to be enclosed within an atrium;
a balloon adapted to be enclosed within a ventricle; and
a device which controls the volumetric expansion and volumetric contraction of the balloon adapted to be enclosed within the atrium and the balloon adapted to be enclosed within the ventricle wherein:
during a first epoch in which atrioventricular valves are closed and aortic and pulmonary valves are open, volumetrically contracting the balloon adapted to be enclosed within the atrium and volumetrically expanding the balloon adapted to be enclosed within the ventricle; and
during a second epoch in which the atrioventricular valves are open and the aortic and pulmonary valves are closed, volumetrically expanding the balloon adapted to be enclosed within the atrium and volumetrically contracting the balloon adapted to be enclosed within the ventricle.

11. The apparatus of claim 10 further comprising wherein the device controls iterating volumetric expansion and volumetric contraction of the balloon adapted to be enclosed within the atrium and the balloon adapted to be enclosed within the ventricle in successive epochs in synchronization with a pacemaker.

12. The apparatus of claim 10 further comprising wherein the device controls iterating volumetric expansion and volumetric contraction of the balloon adapted to be enclosed within the atrium and the balloon adapted to be enclosed within the ventricle in successive epochs in response to input from a controller.

13. The apparatus of claim 10 further comprising wherein the device controls iterating volumetric expansion and volumetric contraction of the balloon adapted to be enclosed within the atrium and the balloon adapted to be enclosed within the ventricle in successive epochs in response to patient activity level.

14. The apparatus of claim 10 further comprising wherein the device controls calculating a first volume of expansion of the balloon adapted to be enclosed within the atrium and calculating a second volume of expansion of the balloon adapted to be enclosed within the ventricle, the first volume of expansion and the second volume of expansion calculated based on at least one of pre-existing blood ejection fraction for each chamber, size of each chamber; and desired output.

15. The apparatus of claim 14 further comprising wherein the device controls configuring the balloon adapted to be enclosed within the atrium for the calculated first volume of expansion and the balloon adapted to be enclosed within the ventricle for the calculated second volume of expansion.

16. The apparatus of claim 14 further comprising wherein the device controls adjusting the calculated first volume of expansion and adjusting the calculated second volume of expansion based on echocardiogram data.

17. The apparatus of claim 14 further comprising wherein the device controls storing data indicative of at least one of: the calculated first volume of expansion, the calculated second volume of expansion, associated volumes of blood ejected from each chamber for each epoch, number of epochs, total volume of blood pumped, and pressure in each chamber.

18. A method for treating a heart to increase blood flow, comprising the steps of:
during a first epoch in which atrioventricular valves are closed and aortic and pulmonary valves are open, volumetrically contracting a balloon enclosed within an atrium; and
during a second epoch in which the atrioventricular valves are open and the aortic and pulmonary valves are closed, volumetrically expanding the balloon enclosed within the atrium.

19. The method of claim 18 further comprising iterating volumetric expansion and volumetric contraction of the balloon enclosed within the atrium in successive epochs in synchronization with sensed timing of the heart.

20. The method of claim 18 further comprising iterating volumetric expansion and volumetric contraction of the balloon enclosed within the atrium in successive epochs in synchronization with a pacemaker.

21. The method of claim 18 further comprising iterating volumetric expansion and volumetric contraction of the balloon enclosed within the atrium in successive epochs in response to input from a controller.

22. The method of claim 18 further comprising iterating volumetric expansion and volumetric contraction of the balloon enclosed within the atrium in successive epochs in response to patient activity level.

23. The method of claim 18 further comprising calculating a volume of expansion of the balloon enclosed within the atrium, the volume of expansion calculated based on at least one of pre-existing blood ejection fraction for a cardiac chamber, size of a cardiac chamber; and desired output of the atrium.

24. The method of claim 23 further comprising configuring the balloon enclosed within the atrium for the calculation of the volume of expansion.

25. The method of claim 23 further comprising adjusting the calculation of the volume of expansion based on echocardiogram data.

26. The method of claim 23 further comprising storing data indicative of at least one of: the calculation of the volume of expansion, associated volumes of blood ejected from each chamber for each epoch, number of epochs, total volume of blood pumped, and pressure in each chamber.

* * * * *